(12) United States Patent
Li et al.

(10) Patent No.: US 8,608,944 B2
(45) Date of Patent: Dec. 17, 2013

(54) CATALYTIC CONVERSION METHOD OF INCREASING THE YIELD OF LOWER OLEFIN

(75) Inventors: Zheng Li, Beijing (CN); Jun Long, Beijing (CN); Shuandl Hou, Beijing (CN); Zhijian Da, Beijing (CN); Chaogang Xie, Beijing (CN); Jiushun Zhang, Beijing (CN); Zhanzhu Zhang, Beijing (CN)

(73) Assignees: Research Institute of Petroleum Processing SINOPEC, Beijing (CN); China Petroleum & Chemical Corporation, Beijing (CN)

( * ) Notice: Subject to any disclaimer, the term of this patent is extended or adjusted under 35 U.S.C. 154(b) by 859 days.

(21) Appl. No.: 12/158,145

(22) PCT Filed: Dec. 19, 2006

(86) PCT No.: PCT/CN2006/003481
§ 371 (c)(1),
(2), (4) Date: Jul. 24, 2008

(87) PCT Pub. No.: WO2007/071177
PCT Pub. Date: Jun. 28, 2007

(65) Prior Publication Data
US 2008/0314799 A1 Dec. 25, 2008

(30) Foreign Application Priority Data
Dec. 23, 2005 (CN) .......................... 2005 1 0132192

(51) Int. Cl.
*C10G 47/32* (2006.01)
*C10G 11/04* (2006.01)
*C10G 49/08* (2006.01)

(52) U.S. Cl.
USPC ...... 208/111.01; 208/107; 208/109; 208/110; 208/118; 208/119; 208/120.01

(58) Field of Classification Search
USPC .......... 585/648, 653, 650, 651; 208/106, 113, 208/121, 122, 120.01, 107, 109, 110, 208/111.01, 118, 119
See application file for complete search history.

(56) References Cited

U.S. PATENT DOCUMENTS 3,249,529 A * 5/1966 Viles ........................ 208/120.1
3,413,212 A * 11/1968 Weisz ...................... 208/120.15

(Continued)

FOREIGN PATENT DOCUMENTS

| CN | 86104433 | 1/1987 |
| CN | 1600757 | 3/2005 |

(Continued)

OTHER PUBLICATIONS

Häussinger, et al., "Hydrogen" in Ullmann's Encyclopedia of Industrial Chemistry, Wiley-VCH, 2002, available on-line Jun. 15, 2000.*

(Continued)

*Primary Examiner* — In Suk Bullock
*Assistant Examiner* — Bradley Etherton
(74) *Attorney, Agent, or Firm* — Novick, Kim & Lee, PLLC; Allen Xue

(57) ABSTRACT

A catalytic conversion process for increasing the light olefin yields, which comprises bringing a hydrocarbon oil feedstock into contact with a catalytic conversion catalyst in a catalytic conversion reactor including one or more reaction zones to carry out the reaction, wherein the hydrocarbon oil feedstock is subjected to the catalytic conversion reaction in the presence of an inhibitor; and separating the reactant vapor optionally containing the inhibitor from the coke deposited catalyst, wherein a target product containing ethylene and propylene is obtained by separating the reactant vapor, and the coke deposited catalyst is stripped and regenerated for recycle use by being returned to the reactor. The process can weaken the further converting reaction of produced light olefins such as ethylene and propylene to 50-70% of the original level by injecting the inhibitor; thereby it can increase the yields of the target products. When vacuum gas oil is used as the feedstock, the yield of ethylene is as high as 8.73 wt % and that of propylene is as high as 29.30 wt %, increasing by 14.4% and 26.6% respectively comparing to those obtained without the inhibitor being injected.

22 Claims, 2 Drawing Sheets

(56) References Cited

U.S. PATENT DOCUMENTS

| | | | |
|---|---|---|---|
| 3,702,886 A | 11/1972 | Argauer et at. | |
| 3,894,934 A * | 7/1975 | Owen et al. | 208/78 |
| 4,002,557 A * | 1/1977 | Owen et al. | 208/120.01 |
| 4,012,455 A * | 3/1977 | Owen et al. | 585/408 |
| 4,035,285 A * | 7/1977 | Owen et al. | 208/120.01 |
| 4,348,272 A * | 9/1982 | Tu | 208/111.15 |
| 4,658,081 A | 4/1987 | Kolts | |
| 4,980,053 A * | 12/1990 | Li et al. | 208/120.01 |
| 6,093,867 A * | 7/2000 | Ladwig et al. | 585/648 |
| 6,106,697 A * | 8/2000 | Swan et al. | 208/77 |
| 6,210,562 B1 | 4/2001 | Xie et al. | |
| 6,222,087 B1 * | 4/2001 | Johnson et al. | 585/651 |
| RE37,789 E * | 7/2002 | Bertus et al. | 208/120.2 |
| 6,538,169 B1 * | 3/2003 | Pittman et al. | 585/653 |
| 6,548,725 B2 | 4/2003 | Froment et al. | |
| 2001/0042701 A1 | 11/2001 | Stuntz et al. | |
| 2002/0195373 A1 * | 12/2002 | Ino et al. | 208/113 |
| 2003/0070963 A1 | 4/2003 | Zimmermann et al. | |
| 2003/0132137 A1 | 7/2003 | Stuntz et al. | |
| 2004/0112793 A1 * | 6/2004 | Dath et al. | 208/109 |
| 2005/0133419 A1 * | 6/2005 | Long et al. | 208/120.01 |

FOREIGN PATENT DOCUMENTS

| | | |
|---|---|---|
| EP | 0171460 A1 | 2/1986 |
| EP | 0229437 A1 | 7/1987 |
| EP | 0171460 B1 | 8/1988 |
| EP | 1046696 A3 | 1/2001 |
| EP | 1508555 A1 * | 2/2005 |
| WO | 0178490 A2 | 10/2001 |
| WO | 0179393 A2 | 10/2001 |
| WO | 0179395 A2 | 10/2001 |

OTHER PUBLICATIONS

Lee, "Catalytic Cracking under Hydrogen Fluidization" in Ind. Eng. Chem. Res., 1989, 28, 920-925—month unknown.*

Chen, J., "Catalytic Cracking Technology and Engineering", 2nd Ed., SINOPEC Press, 2005, pp. 151-152.

* cited by examiner

CATALYTIC CONVERSION METHOD OF INCREASING THE YIELD OF LOWER OLEFIN

RELATED APPLICATIONS

This application is a national stage application (under 35 U.S.C. §371) of PCT/CN2006/003481, filed Dec. 19, 2006, which claims benefit of Chinese application 200510132192.2, filed Dec. 23, 2005.

FIELD OF THE INVENTION

The present invention pertains to a catalytic conversion process of hydrocarbon oils. More particularly, it is a process for producing light olefins such as ethylene and propylene by using the catalytic conversion of hydrocarbon oils in the presence of a catalyst.

BACKGROUND OF THE INVENTION

The conventional process for producing light olefins from petroleum hydrocarbons is the steam cracking process, the mechanism of which is the steam cracking mechanism of the free radical of hydrocarbons; therefore, the ethylene yield of this process is relatively high. Generally speaking, the mass ratio of propylene to ethylene produced by the steam cracking of naphtha is about 0.43. However, the mass ratio of propylene to ethylene desired in the market is over 0.70. Although the propylene yield can be increased by adequately lowering the reaction severity, the mass ratio of propylene to ethylene is not suitable to exceed 0.65, otherwise, the total yield of light olefins may be decreased and the profit of the process will shrink in consequence. In addition, the feedstock suitable for the steam cracking is light petroleum hydrocarbon such as ethane, propane, butane, natural gas, naphtha or light cycle oil. But the supply amount of light hydrocarbons is limited along with the trend that the crude oil is becoming heavier, so that researchers have to shift their focus to use a wider range of feedstock including heavy petroleum hydrocarbons for producing light olefins.

Over past few years, some patent documents have disclosed the processes for producing light olefins via the catalytic cracking reaction on acidic zeolite by using heavy petroleum hydrocarbons, naphtha, C4-C6 light hydrocarbons and the like as the feedstock. Compared to the steam cracking, the processes of this kind have two superiorities. One is that the mass ratio of propylene to ethylene is high in the gaseous product since the reaction of hydrocarbons on the acidic zeolitic catalyst follows the carbenium ion mechanism. The other is that by utilizing the mature engineering and technology of the fluidized catalytic cracking, the processes of this kind not only can treat light hydrocarbon feedstock, but also can treat heavy hydrocarbon feedstock.

U.S. Pat. No. 4,980,053 disclosed a catalytic cracking process for producing propylene and butylene. This process used a fluidized bed or moving bed reactor and a solid acidic catalyst to carry out the reaction at the reaction temperature of 500-650° C. under the feed weight hourly space velocity of 0.2-20 $h^{-1}$ with the mass ratio of catalyst to feedstock being 2-12. In its Example 1, the reaction was carried out at 580° C. with a catalyst of ZSM-5 as the active component and kaolin as the support using vacuum gas oil as the feedstock, and it had yields of 5.89 wt % for ethylene, 21.56 wt % for propylene and 15.64 wt % for butylene.

U.S. Pat. No. 6,210,562 disclosed a catalytic pyrolysis process for producing ethylene and propylene. In this process, the preheated heavy petroleum hydrocarbons were brought into contact with a catalyst containing pillared interlayered clay zeolite and/or phosphorous and aluminum or magnesium or calcium modified high silica zeolite having pentasil structure in the presence of high temperature steam in a riser or a downflow transfer-line reactor, and the catalytic pyrolysis reaction was carried out at the temperature of 650-750° C. under the reaction pressure of $1.5-4.0\times10^5$ Pa for the reaction time of 0.2-5 seconds with the mass ratio of catalyst to feedstock being 15-40:1 and the mass ratio of steam to feedstock being 0.3-1:1. Both ethylene and propylene were obtained in yields over 18 wt % in this process.

U.S. Pat. No. 6,106,697 disclosed a process for selectively producing C2-C4 olefins by using gas oil or residual oil as the feedstock to carry out the catalytic cracking reaction in a two stage reactor. Gas oil or residual oil was brought into contact with a large pore zeolitic catalyst in the first stage reactor to carry out the catalytic cracking reaction under the conventional catalytic cracking conditions to give products with different boiling ranges including naphtha fraction. The naphtha fraction obtained in the first stage reactor entered the second stage reactor and was brought into contact with a medium pore shape-selective zeolitic catalyst to carry out the further reaction at the reaction temperature of 500-650° C. with the mass ratio of catalyst to feedstock of 4-10:1 under the hydrocarbon partial pressure of 70-280 kPa to give C2-C4 olefins.

To sum up, the main means for increasing yields of ethylene, propylene and butylene in the prior arts are the use of higher reaction temperatures, higher catalyst to oil ratios, and larger amounts of injected steam than those used in the conventional catalytic cracking and the use of catalysts containing medium pore shape-selective zeolite having an average pore diameter less than about 0.7 nanometers. All the above means can intensify the cracking reactions of petroleum hydrocarbons, i.e., all the prior arts attain the objective for increasing yields of ethylene, propylene and butylene by intensifying the formation reaction of ethylene, propylene and butylene. All along, the ordinary skilled in the art generally considered propylene as a stable reaction product under the catalytic cracking reaction conditions, for example, there is a statement on the page 152 of the book "Catalytic Cracking Technology and Engineering (2nd Ed)" by Chen Junwu, China PetroChemical Press, Mar. 1, 2005 that "propylene is a stable product and essentially it does not convert any longer at high feedstock conversion". Nevertheless, the inventor has surprisingly discovered via laboratory study that propylene possesses a notable reactivity under the reaction conditions for the catalytic conversion of petroleum hydrocarbons to produce light olefins in the presence of an acidic zeolite and it can be converted into other hydrocarbons, hydrogen, and coke rapidly in a large quantities, leading to a reduction of the propylene yield on the contrary.

SUMMARY OF THE INVENTION

The object of the present invention is to provide a catalytic conversion process for increasing light olefin yields on the basis of the inventor's discovery. This process will increase light olefin yields, especially propylene yield, by inhibiting the subsequent converting reaction of light olefins such as propylene after their formation with the use of an inhibitor.

The process provided by the present invention comprises bringing a hydrocarbon oil feedstock into contact with a catalytic conversion catalyst in a catalytic conversion reactor including one or more reaction zones to carry out the reaction, wherein the hydrocarbon oil feedstock is subjected to the catalytic conversion reaction in the presence of an inhibitor; and separating the reactant vapor optionally containing the inhibitor from the coke deposited catalyst, wherein a target product containing ethylene and propylene is obtained by separating the reactant vapor, and the coke deposited catalyst is stripped and regenerated for recycle use by being returned to the reactor.

Said hydrocarbon oil feedstock of the present invention is one selected from the group consisting of petroleum hydrocarbon oils, mineral oils, synthetic oils and mixtures thereof. The petroleum hydrocarbon oil is one selected from the group consisting of the C4-C6 fraction, naphtha, light cycle oil, vacuum gas oil, coker gas oil, deasphalted oil, unconverted oil of hydrogenation, atmospheric residual oil, vacuum residual oil, crude oil and mixtures thereof. The mineral oil is one selected from the group consisting of coal liquefied oil, oil sand bitumen, shale oil and mixtures thereof. The synthetic oil is a distillate produced via the F-T synthesis process from coal, natural gas, or asphalt.

Said catalytic conversion catalyst of the present invention comprises zeolite, inorganic oxide, and optional clay, and the contents of components are 10-50 wt % for zeolite, 5-90 wt % for inorganic oxide and 0-70 wt % for clay respectively.

As an active component, the zeolite is selected from medium pore shape-selective zeolite having an average pore diameter less than about 0.7 nanometers and optional large pore zeolite having an average pore diameter more than about 0.7 nanometers. The medium pore zeolite comprises 25-100%, preferably 50-100% by the total weight of active components. The large pore zeolite comprises 0-75%, preferably 0-50% by the total weight of active components. The medium pore zeolite is selected from the ZSM series zeolite and/or the ZRP zeolite, or the above medium pore zeolite modified by nonmetal elements such as phosphor and/or transition metal elements such as iron, cobalt and nickel. The more detailed description of the ZRP zeolite can be referred to U.S. Pat. No. 5,232,675. The ZSM series zeolite is one selected from the group consisting of ZSM-5, ZSM-8, ZSM-11, ZSM-12, ZSM-23, ZSM-35, ZSM-38, ZSM-48, other zeolites with similar structure, and mixtures thereof. The more detailed description of ZSM-5 can be referred to U.S. Pat. No. 3,702,886. The large pore zeolite is one selected from the group consisting of rare earth Y (REY), rare earth HY (REHY), ultrastable Y obtained by different processes, high-silica Y and mixtures thereof. All of these zeolites are commerically available.

As a matrix, the inorganic oxide is selected from silica ($SiO_2$) and/or alumina ($Al_2O_3$).

As a support, clay is selected from kaolin and/or halloysite.

The reaction zone of the catalytic conversion reactor of the present invention is selected from one or more risers, one or more fluidized beds, one or more downers, riser+fluidized bed, riser+downer, downer+fluidized bed, and modified forms thereof, wherein the riser may be a unidiameter riser or a riser having a varying diameter.

The inhibitor of the present invention is or contains one selected from a substance having a hydrogen-donating ability, a substance having the reducibility, a substance having an adsorbability on the active center of acidic catalysts and mixtures thereof; wherein the substance having a hydrogen-donating ability is or contains one selected from the group consisting of hydrogen, tetrahydronaphthalene, decahydronaphthalene, catalytic cracking dry gas, coking dry gas and mixtures thereof; the substance having a reducibility is or contains carbon monoxide; the substance having an adsorbability on the active center of acidic catalysts is or contains one selected from the group consisting of methanol, ethanol, ammonia, pyridine and mixtures thereof.

The injection site for the inhibitor of the present invention includes any part of a feed line for the hydrocarbon oil feedstock, a delivery line for the regenerated catalyst, the reaction zone of the reactor, a disengager for separating the reactant vapor from the coke deposited catalyst and a stripper for stripping the coke deposited catalyst.

When the inhibitor is injected from the reaction zone of the reactor, the inhibitor is preferably injected downstream of the catalyst inlet of the reaction zone.

In the case that a reactor having several reaction zones is used, the inhibitor is preferably injected from the site between the reaction zones. For example, upon using riser+fluidized bed, the inhibitor is preferably injected from the site between the riser and the fluidized bed. However, since the properties of the feedstock and the catalyst are different, it is not excluded that the inhibitor is injected from other sites downstream of the catalyst inlet of the riser.

Upon using a riser having a varying diameter, the inhibitor is preferably injected from the diameter-varying part of the riser. However since the properties of the feedstock and the catalyst are different, it is not excluded that the inhibitor is injected from other sites downstream of the catalyst inlet of the riser.

The ratio of the inhibitor to the hydrocarbon oil feedstock is 0.001-15 wt %, preferably 0.003-10 wt % of the hydrocarbon oil feedstock.

The inhibitor of the present invention can be either injected at one site or simultaneously at several sites, and the inhibitor is injected at each site in an amount of 0-100 wt % of the total amount of the injected inhibitor.

The inhibitor of the present invention is recycled in an amount of 0-100 wt % of the inhibitor separated from the reaction product, that is, the inhibitor can be used with no recycling, partial recycling or complete recycling.

The separation procedure of the reactant vapor and the inhibitor of the present invention is carried out in an apparatus commonly used in the prior art.

In the process of the present invention, the reaction temperature of the hydrocarbon oil feedstock, which is specially defined as the outlet temperature of the last reaction zone of the reactor, is 500-700° C., preferably 550-650° C. The pressure of the disengager for separating the reactant vapor from the coke deposited catalyst is $1.5-4\times10^5$ Pa, preferably $1.5-3.5\times10^5$ Pa. The reaction time is 0.5-10 seconds, preferably 1-5 seconds. The mass ratio of catalyst to hydrocarbon oil feedstock is 6-40, preferably 10-30. The mass ratio of steam to hydrocarbon oil feedstock is 0.1-1:1, preferably 0.2-0.6:1.

Comparing to the prior art, the present invention possesses the following advantages:

1. The process of the present invention can weaken the further converting reaction of produced light olefins to 50-70% of the original level by injecting the inhibitor; thereby it can increase the yields of the target products. When vacuum gas oil is used as the feedstock, the yield of ethylene is as high as 8.73 wt % and that of propylene is as high as 29.30 wt %, increasing by 14.4% and 26.6% respectively comparing to those obtained without the inhibitor being injected.

2. The present invention can reduce the amount of the steam used by injecting the inhibitor into the reactor, and it can further decelerate the hydrothermal deactivation of the catalyst to a certain extent and prolong the service life of the catalyst.

3. The process of the present invention has a wide source of feedstock, including C4-C6 fraction, naphtha fraction and a variety of heavy hydrocarbons. In addition, the present invention has a relatively broad range of utilization since the existing units can be used after their slight modification.

DESCRIPTION OF THE PREFERRED EMBODIMENTS

The present invention may have many embodiments according to the different properties of the feedstock and the catalyst since the inhibitor of the present invention can be injected at different sites. The process of the present invention will be illustrated in details in conjunction with FIGS. 1 and 2 by reference to the following embodiments of the inhibitor being injected into the reaction zone from the feed nozzle and used in a recycling operation mode, and the inhibitor being injected from the stripper and used in a once-through mode, respectively, but the present invention is not intended to be limited thereby.

Figure 1:
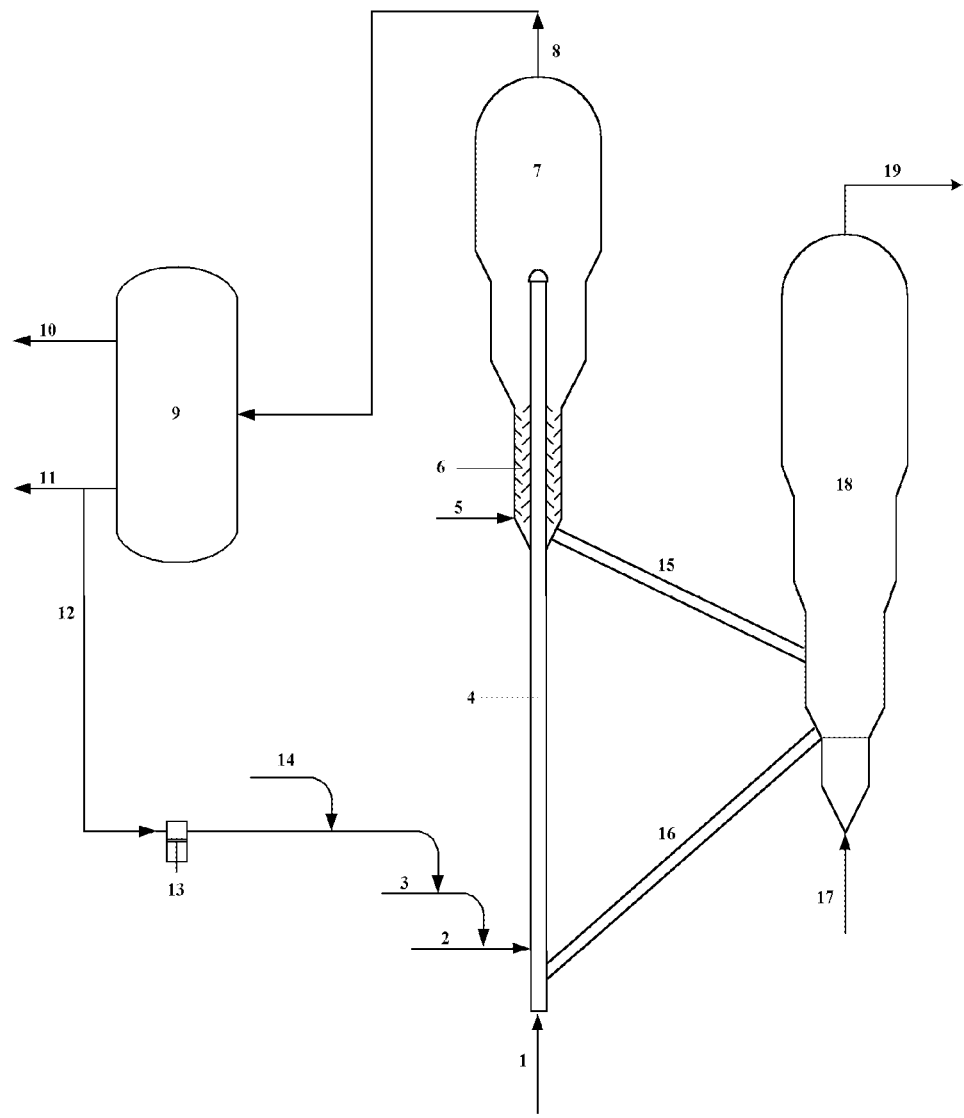
FIG. 1 is a schematic flow sheet of the catalytic conversion process provided by the present invention for increasing the light olefin yields, wherein the inhibitor is injected into the reaction zone from the feed nozzle and used in a recycling operation mode.

FIG. 1 is a schematic flow sheet illustrating that the inhibitor is injected into the reaction zone from the feed nozzle and used in a recycling operation mode. In the procedure shown by this figure, the hot regenerated catalyst enters the bottom of the riser 4 via the delivery line 16 for the regenerated catalyst and flows upwards in an accelerating speed with the help of the pre-lifting medium injected from the line 1. The preheated hydrocarbon oil feedstock from the line 2, the atomizing steam from the line 3 and the inhibitor from the line 14 are mixed in a certain proportion, then the mixture is injected into the riser 4 and brought into contact with the hot catalyst in the presence of the inhibitor to carry out the reaction for the reaction time of 0.5-10 seconds at the outlet temperature for the riser 4 of 500-700° C. under the pressure for the disengager 7 of $1.5\text{-}4\times10^5$ Pa with the mass ratio of catalyst to hydrocarbon feedstock being 6-40. The mixture of the reactant vapor, the inhibitor and the catalyst rise along the riser to the outlet of the riser and then enters the disengager 7, wherein the reactant vapor optionally containing the inhibitor is separated from the coke deposited catalyst. The reactant vapor and the inhibitor are sent to the subsequent separation system 9 via the line 8 for the further separation, and the reaction product is withdrawn from the line 10 after separation and further separated to obtain the target products propylene, ethylene and the like as well as naphtha, light cycle oil, heavy oil and the like (not shown in the figure). One part of the inhibitor is withdrawn via the line 11; and the other part of the inhibitor is recycled by entering the separator 13 via the line 12 for a further separation and refinement, mixing with the fresh inhibitor from the line 14 followed by entering the reaction zone together with the atomizing steam via the line 3. The coke deposited catalyst enters the stripper 6, into which the stripping steam is injected via the line 5 and brought into countercurrent contact with the coke deposited catalyst to strip out the reaction product entrained by the coke deposited catalyst as much as possible. The stripped catalyst is sent to the regenerator 18 via the delivery line 15 for the spent catalyst and is regenerated by burning out the coke deposited on it. An oxygen-containing gas such as air is injected into the regenerator 18 via the line 17 and the regeneration flue gas is withdrawn via the line 19. The regenerated catalyst is recycled to the riser 4 via the delivery line 16 for the regenerated catalyst.

Figure 2:
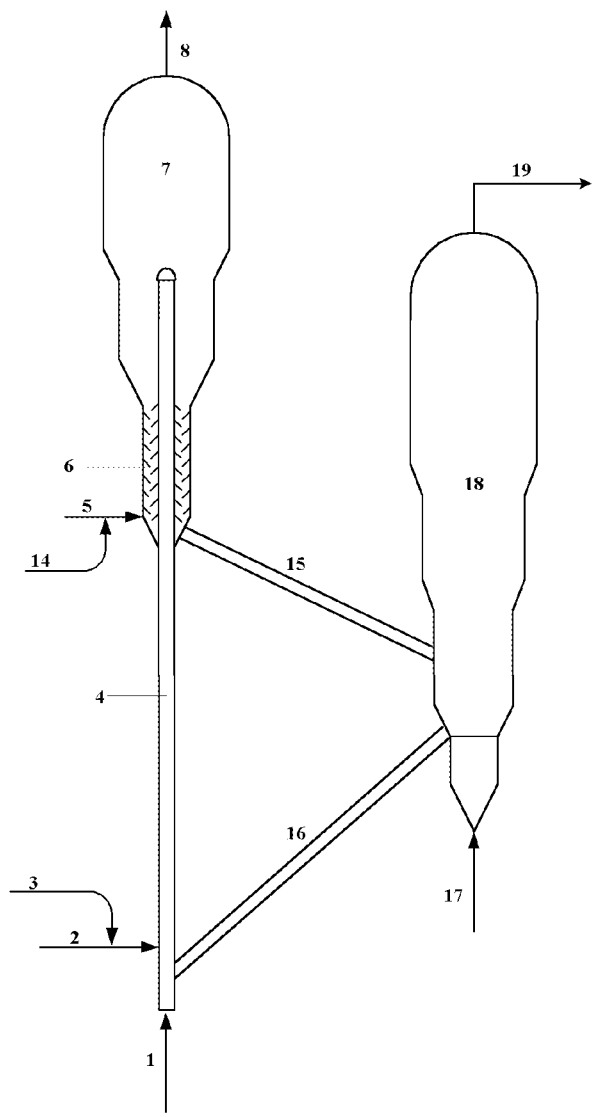
FIG. 2 is a schematic flow sheet of the catalytic conversion process provided by the present invention for increasing the light olefin yields, wherein the inhibitor is injected from the stripper and used in a once-through mode.

FIG. 2 is a schematic flow sheet illustrating the inhibitor is injected from the stripper and used in a once-through mode. In the procedure shown by this figure, the hot regenerated catalyst enters the bottom of the riser 4 via the delivery line 16 for the regenerated catalyst, and flows upwards in an accelerating speed with the help of the pre-lifting medium injected from pipe 1. The preheated hydrocarbon oil feedstock from the line 2 and the atomizing steam from the line 3 are mixed in a certain proportion, then the mixture is injected into the riser 4 and brought into contact with the hot catalyst to carry out the reaction for the reaction time of 0.5-10 seconds at the outlet temperature for the riser 4 of 500-700° C. under the pressure for the disengager 7 of $1.5\text{-}4\times10^5$ Pa with the mass ratio of catalyst to hydrocarbon oil feedstock being 6-40. The mixture of the reactant vapor and the catalyst rise along the riser to the outlet of the riser and then enters the disengager 7, wherein the reactant vapor is separated from the coke deposited catalyst. The reactant vapor is sent to the subsequent separation system 9 via the line 8 to complete the product separation. The coke deposited catalyst enters the stripper 6, into which the stripping steam and the inhibitor from the line 14 are injected via the line 5 and brought into countercurrent contact with the coke deposited catalyst to strip out the reaction product entrained by the coke deposited catalyst as much as possible. The inhibitor enters the disengager 7 via the stripper 6 to inhibit the further converting reactions of ethylene and propylene and then enters the product separation system together with the reactant vapor. The stripped catalyst is sent to the regenerator 18 via the delivery line 15 for the spent catalyst and is regenerated by burning out the coke deposited on it. An oxygen-containing gas such as air is injected into the regenerator 18 via the line 17 and the regeneration flue gas is withdrawn via the line 19. The regenerated catalyst is recycled to the riser 4 via the delivery line 16 for the regenerated catalyst.

The process provided by the present invention will be further described by way of the following examples, but the present invention is not subjected to any limitation thereby.

The catalyst used in the examples is a commercial product available from SINOPEC Catalyst Qilu Subcompany, with a trade mark of MMC-2. The feedstock A used in the examples is a pure propylene with the propylene concentration over 99.9 vol % and the feedstock B is a vacuum gas oil, whose main properties are shown in Table 1.

Example 1

This example shows the catalytic reactivity of the light olefin in a bench fixed fluidized bed reactor using carbon monoxide as the inhibitor according to the process of the present invention.

The experiment was conducted in a batch operation mode with the feedstock A as the feedstock. The feedstock, the inhibitor and the atomizing steam were heated by a preheating furnace to about 350° C. and then fed to the bottom of the fluidized bed reactor via the feed nozzle, coming into contact with the hot catalyst to carry out the catalytic conversion reaction. The reactant vapor and the inhibitor were separated from the coke deposited catalyst and then entered the product separation system, and the reactant vapor was further separated into a gas product and a liquid product. After the reaction was finished, the stripping step was conducted to strip out the hydrocarbon products adsorbed on the spent catalyst by steam. After stripping, an oxygen-containing gas was introduced into the reactor to carry out the regeneration of the spent catalyst, and the catalyst can be used in the next reaction after its regeneration. The main operating conditions and results of the experiment are listed in Table 2.

Example 1'

This example shows the catalytic reactivity of the light olefin in the case of no inhibitor being injected during the reaction, aiming to further demonstrate the practical effect of the present invention. This example has a different experiment phenomenon discovered by the inventors in the laboratory from those as known by the conventional knowledge.

The feedstock A was used as the feedstock in the experiment. The used reactor, the main experiment steps and other operating conditions were the same as those of Example 1. The main operating conditions and results are listed in Table 2.

It can be seen from the comparison between the experiment results of Example 1 and Example 1' in Table 2 that propylene had a considerable high reactivity under the conventional reaction conditions for producing light olefins by the catalytic conversion and the conversion of propylene is as high as 55.19 wt %. This was quite different from the knowledge of most researchers. The process of the present invention can greatly inhibit the converting reaction of propylene. The conversion of propylene in Example 1 is reduced by 22.8 percentages.

Example 2

The present example shows the catalytic reactivity of the light olefin in a bench fixed fluidized bed reactor using hydrogen as the inhibitor according to the process of the present invention.

The feedstock A was used as the feedstock in the experiment. The used reactor and the main experiment steps were the same as those of Example 1. The main operating conditions and results are listed in Table 2.

Example 2'

This example shows the catalytic reactivity of the light olefin in the case of no inhibitor being injected during the reaction, aiming to further demonstrate the practical effect of the present invention. This example has a different experiment phenomenon discovered by the inventors in the laboratory from those as known by the conventional knowledge.

The feedstock A was used as the feedstock in the experiment. The used reactor, the main experiment steps and other operating conditions were the same as those of Example 2. The main operating conditions and results are listed in Table 2.

It can be seen from the comparison between the experiment results of Example 2 and Example 2' in Table 2 that propylene had a considerable high reactivity under the conventional reaction conditions for producing light olefins by the catalytic conversion and the conversion of propylene is as high as 64.01 wt %. This was quite different from the knowledge of most researchers. The process of the present invention can greatly inhibit the further converting reaction of propylene. The conversion of propylene in Example 2 is reduced by 29.97 percentages.

Example 3

This example shows the catalytic reactivity of the light olefin in a bench fixed fluidized bed reactor using ammonia as the inhibitor according to the process of the present invention.

The feedstock A is used as the feedstock in the experiment. The used reactor and the main experiment steps were the same as those of Example 1. The main operating conditions and results are listed in Table 2. It can be seen from Table 2 that the conversion of propylene was only 38.30 wt %.

Example 4

This example shows the catalytic conversion of heavy hydrocarbons to produce ethylene and propylene in the case of the inhibitor being injected at different sites according to the process of the present invention.

The experiment was conducted with the feedstock B as the feedstock and methanol as the inhibitor to carry out the catalytic conversion experiment in a pilot riser unit in a continuous reaction-regeneration operation. The riser had an inner diameter of 16 mm and a height of 6 m, and there was a fluidized bed reaction zone, having an inner diameter of 64 mm and a height of 0.3 m, above the outlet of the riser reaction zone.

The experiment was conducted in a once-through operation mode. The inhibitor was injected from the feed nozzle. The regenerated catalyst having a temperature around 700° C. entered the bottom of the riser reaction zone via the pipe for the regenerated catalyst and flew upwards with the help of the pre-lifting steam. The feedstock was preheated in a preheating furnace to about 350° C. and mixed with the atomizing steam and the inhibitor. The mixture sequentially entered the riser reaction zone and the fluidized bed reaction zone via the feed nozzle, coming into contact with the hot catalyst to carry out the catalytic conversion reaction. The reactant vapor, the inhibitor, the steam and the coke deposited catalyst entered the disengager from the outlet of the fluidized bed reaction zone. The reactant vapor and the inhibitor were rapidly separated from the catalyst in the disengager. The reactant vapor was further separated into a gas product and a liquid product, and the spent catalyst entered the stripper by the gravity force. The stripping steam stripped out the hydrocarbon products entrained by the spent catalyst and then entered the gas-liquid separation system via the fluidized bed reaction zone. The stripped spent catalyst entered the regenerator and was regenerated by way of contacting heated air. The regenerated catalyst was stripped by steam in the delivery line to remove the non-hydrocarbon gas impurities entrained by the regenerated catalyst. The stripped regenerated catalyst returned to the riser reaction zone for recycling.

The main operating conditions and results of the experiment are listed in Table 3. It can be seen from Table 3 that the yields of ethylene and propylene are as high as 8.73 wt % and 29.30 wt %, respectively.

Comparative Example

This example shows the catalytic conversion of heavy hydrocarbons as the feedstock to produce ethylene and propylene in the case of no inhibitor being injected.

The feedstock B was used as the feedstock in the experiment. The used reactor, the main experiment steps and other operating conditions were the same as those of Example 4. The main operating conditions and results are listed in Table 3. The partial pressures of the feedstock B at the inlet of the riser in example 4 and the comparative example were equal to ensure that the conversion of the feedstock was not affected by the variation of the partial pressure.

In can be seen from the comparison between the experiment results of the example 4 and the comparative example that on the basis of the prior art for the catalytic conversion of petroleum hydrocarbons for producing light olefins, higher yields of ethylene and propylene can be achieved according to the process of the present invention. Comparing to the comparative example, wherein the same reaction conditions were used and no inhibitor was injected, the yields of ethylene and propylene increased by 14.4% and 26.6%, respectively.

Example 5

This example shows the catalytic conversion of heavy hydrocarbons to produce ethylene and propylene in the case of the inhibitor being injected at different sites according to the process of the present invention.

The experiment was conducted with the feedstock B as the feedstock and hydrogen as the inhibitor, which was injected from the distributor of the stripping steam. The reaction unit and the main steps used in the experiment were the same as those in Example 4, and the main operating conditions and results are listed in Table 3. It can be seen from Table 3 that the yields of ethylene and propylene are as high as 8.73 wt % and 28.55 wt %, respectively.

Example 6

This example shows the catalytic conversion of heavy hydrocarbons to produce ethylene and propylene in the case of the inhibitor being injected at different sites according to the process of the present invention.

The experiment was conducted with the feedstock B as the feedstock and decahydronaphthalene as the inhibitor, which was injected from the distributor of the pre-lifting steam. The reaction unit and the major steps used in the experiment were the same as those in Example 4, and the main operating conditions and results are listed in Table 3. It can be seen from Table 3 that the yields of ethylene and propylene are as high as 8.15 wt % and 27.88 wt %, respectively.

Example 7

This example shows the catalytic conversion of heavy hydrocarbons to produce ethylene and propylene in the case of the inhibitor being a self-produced dry gas, and it being injected from the feed nozzle and used in a recycling operation mode according to the process of the present invention.

The experiment was conducted with the feedstock B as the feedstock. The reaction unit and the main steps used in the experiment were the same as those in Example 4, and the main operating conditions and results are listed in Table 3. It can be seen from Table 3 that the yields of ethylene and propylene are as high as 8.29 wt % and 28.52 wt %, respectively.

TABLE 1

| Code of Feedstock | B |
|---|---|
| Density(20° C.), g/cm$^3$ | 0.8617 |
| Kinematic viscosity(80° C.), mm$^2$/s | 7.33 |
| Kinematic viscosity(100° C.), mm$^2$/s | 4.864 |
| Solidifying point, ° C. | 42 |
| Aniline point, ° C. | 105.3 |
| Molecular weight (calculated) | 391 |
| Carbon residue, wt % | 0.02 |

TABLE 1-continued

| Code of Feedstock | B |
|---|---|
| H/C mole ratio | 1.895 |
| Basic nitrogen compounds, ppm | 206 |
| Element composition | |
| C, wt % | 86.3 |
| H, wt % | 13.63 |
| N, ppm | 560 |
| S, ppm | 810 |
| SARA, wt % | |
| Saturates | 85.0 |
| Aromatics | 12.0 |
| Resins | 3.0 |
| Asphaltenes | <0.1 |
| Metal content, ppm | |
| Ca | — |
| Cu | <0.1 |
| Fe | 2 |
| Na | 1.8 |
| Ni | <0.1 |
| V | <0.1 |
| Distillation, ° C. | |
| Initial boiling point | 286 |
| 5% | 343 |
| 10% | 368 |
| 30% | 410 |
| 50% | 437 |
| 70% | 465 |
| 90% | 498 |
| 95% | 512 |

TABLE 2

| Item | Ex 1 | Ex 1' | Ex 2 | Ex 2' | Ex 3 |
|---|---|---|---|---|---|
| Operating conditions | | | | | |
| Reaction temperature, ° C. | 620 | 620 | 580 | 580 | 600 |
| Reaction time, seconds | 1.37 | 1.38 | 0.74 | 0.75 | 1.10 |
| Pressure of disengager, 10$^5$ Pa | 2.1 | 2.1 | 1.8 | 1.8 | 1.9 |
| Catalyst/feedstock mass ratio | 20 | 20 | 10 | 10 | 30 |
| Inhibitor/feedstock ratio, wt % | 0.56 | 0 | 0.0045 | 0 | 4.5 |
| Product distribution, wt % | | | | | |
| Dry gas | 6.68 | 8.12 | 6.65 | 6.31 | 7.19 |
| C4 + Propane | 15.96 | 28.29 | 17.61 | 24.73 | 19.25 |
| Naphtha | 8.02 | 15.56 | 9.09 | 29.68 | 9.88 |
| Light cycle oil | 0.19 | 1.81 | 0.34 | 1.77 | 0.52 |
| Heavy oil | — | 0.18 | — | 0.31 | |
| Coke | 1.54 | 1.23 | 0.35 | 1.46 | 1.46 |
| Propylene conversion, wt % | 32.39 | 55.19 | 34.04 | 64.01 | 38.30 |

The propylene conversion is defined as ☐

$$\text{Propylene conversion (wt \%)} = \frac{\text{Propylene in feed (g)} - \text{Propylene in product (g)}}{\text{Propylene in feed (g)}} \times 100\%$$

TABLE 3

| Item | Ex 4 | Comparative Example | Ex 5 | Ex 6 | Ex 7 |
|---|---|---|---|---|---|
| Operating condition | | | | | |
| Reaction temperature, °C. | 620 | 620 | 650 | 580 | 615 |
| Total reaction time, seconds | 2.9 | 2.9 | 1.8 | 4.2 | 3.8 |
| Pressure of disengager, $10^5$ Pa | 2.7 | 2.7 | 2.1 | 1.9 | 2.3 |
| Catalyst/feedstock mass ratio | 20 | 20 | 10 | 30 | 15 |
| Inhibitor/feedstock ratio, wt % | 1.5 | 0 | 0.0045 | 5.0 | 0.1 |
| Product distribution, wt % | | | | | |
| Gaseous products, wherein | 66.65 | 58.91 | 64.63 | 63.21 | 65.73 |
| Ethylene | 8.73 | 7.63 | 8.73 | 8.15 | 8.29 |
| Propylene | 29.30 | 23.14 | 28.55 | 27.88 | 28.52 |
| Naphtha | 18.56 | 20.51 | 18.08 | 19.29 | 18.52 |
| Light cycle oil | 6.07 | 9.43 | 6.82 | 8.94 | 7.99 |
| Heavy oil | 2.30 | 3.69 | 2.37 | 3.14 | 3.79 |
| Coke | 6.42 | 8.18 | 8.10 | 5.42 | 3.97 |

The invention claimed is:

1. A catalytic conversion process for increasing light olefin yield, comprising the steps of:
   bringing a hydrocarbon oil feedstock comprising vacuum gas oil into contact with a catalytic conversion catalyst in a catalytic conversion reactor, wherein the catalyst is introduced through a catalyst inlet and comprises a medium pore shape-selective zeolite having an average pore diameter less than about 0.7 nanometers and the catalytic conversion reactor comprises one or more reaction zones;
   injecting an inhibitor into the catalytic conversion reactor through one or more injection sites wherein the inhibitor inhibits a conversion of propylene in the catalytic conversion reactor;
   maintaining in said catalytic conversion reactor an outlet temperature of 500-700° C., a reaction time of 0.5-10 seconds, and a weight ratio of said inhibitor to the hydrocarbon oil feedstock of 0.001-15 wt %; and
   obtaining a coke deposited catalyst and a product stream containing ethylene and propylene, wherein the step of injecting the inhibitor increases the yield of propylene in the product stream.

2. The process according to claim 1, wherein said hydrocarbon oil feedstock further comprises one or more components chosen from petroleum hydrocarbon oils, mineral oils, synthetic oils,
   wherein said petroleum hydrocarbon oil is chosen from coker gas oil, deasphalted oil, unconverted oil of hydrogenation, atmospheric residual oil, vacuum residual oils, and crude oil,
   wherein said mineral oil is chosen from coal liquefied oil, oil sand bitumen, and shale oil,
   wherein said synthetic oil is a distillate produced via the F-T synthesis process from coal, natural gas, or asphalt.

3. The process according to claim 1, wherein said catalytic conversion catalyst comprises 10-50 wt % of zeolite, 5-90 wt % of inorganic oxide, and 0-70 wt % of clay.

4. The process according to claim 3, wherein said medium pore zeolite is chosen from the ZSM series zeolite, ZRP zeolite, and a mixture thereof, wherein the ZSM series zeolite is chosen from ZSM-5, ZSM-8, ZSM-11, ZSM-12, ZSM-23, ZSM-35, ZSM-38, ZSM-48, and mixtures thereof.

5. The process according to claim 1, wherein the catalytic conversion reactor comprises one or more risers, or one or more fluidized beds, or one or more downers, or a riser and a fluidized bed, or a riser and a downer, or a downer and a fluidized bed, wherein the riser is a unidiameter riser or a riser having a varying diameter.

6. The process according to claim 1, wherein said inhibitor comprises one chosen from a substance having a hydrogen-donating ability, a substance having an ability to reduce another compound, and a substance having an adsorbability on an active center of acidic catalysts, and mixtures thereof.

7. The process according to claim 6, wherein said substance having a hydrogen-donating ability is chosen from hydrogen, tetrahydronaphthalene, decahydronaphthalene, catalytic cracking dry gas, coking dry gas, and mixtures thereof.

8. The process according to claim 6, wherein said substance having an ability to reduce another compound is carbon monoxide.

9. The process according to claim 6, wherein said substance having an adsorbability on the active center of acidic catalysts is chosen from methanol, ethanol, ammonia, pyridine and mixtures thereof.

10. The process according to claim 1, wherein the injection site for the inhibitor is located in a feed line for the hydrocarbon oil feedstock, a delivery line for the regenerated catalyst, the reaction zone of the reactor, a disengager for separating a reactant vapor from the coke deposited catalyst, and a stripper for stripping the coke deposited catalyst.

11. The process according to claim 1, wherein said injection site for the inhibitor located downstream of the catalyst inlet.

12. The process according to claim 1, wherein said injection site for the inhibitor is located between two adjacent reaction zones.

13. The process according to claim 12, wherein said two adjacent reaction zones are a riser and a fluidized bed.

14. The process according to claim 1, wherein said catalytic conversion reactor comprises a riser having a varying diameter and the injection site for the inhibitor is located in the riser.

15. The process according to claim 1, wherein the weight ratio of said inhibitor to the hydrocarbon oil feedstock is 0.003-10 wt % based on the weight of the hydrocarbon oil feedstock.

16. The process according to claim 1, wherein said inhibitor is injected through one injection site or is injected simultaneously at a plurality of injection sites.

17. The process according to claim 1, wherein the reaction conditions comprise: the pressure of a disengager for separating the product stream from the coke deposited catalyst being 1.5-4×$10^5$ Pa, the weight ratio of the catalyst to the hydrocarbon oil feedstock being 6-40, weight ratio of steam to the hydrocarbon oil feedstock being 0.1-1:1.

18. The process according to claim 17, wherein the reaction conditions comprise: the outlet temperature of the last reaction zone of the reactor being 550-650° C., the pressure of the disengager for separating the reactant vapor from the coke deposited catalyst being $1.5$-$3.5\times10^5$ Pa, the reaction time being 1-5 seconds, the weight ratio of the catalyst to the hydrocarbon oil feedstock being 10-30, the weight ratio of steam to the hydrocarbon oil feedstock being 0.2-0.6:1.

19. The process according to claim 1, wherein said reaction zone of the catalytic conversion reactor comprises a riser and a fluidized bed, and said inhibitor is methanol and used in a once-through operation mode in the catalytic conversion reactor.

20. The process according to claim 1, wherein said reaction zone of the catalytic conversion reactor comprises a riser and a fluidized bed, and said inhibitor is hydrogen and used in a once-through operation mode in the catalytic conversion reactor.

21. The process according to claim 1, wherein said reaction zone of the catalytic conversion reactor comprises a riser and a fluidized bed, and said inhibitor is decahydronaphthalene and used in a once-through operation mode in the catalytic conversion reactor.

22. The process according to claim 1, wherein said reaction zone of the catalytic conversion reactor comprises a riser and a fluidized bed, and said inhibitor is a dry gas self-produced from the catalytic conversion reactor and is used in a recycling operation mode in the catalytic conversion reactor.

* * * * *

UNITED STATES PATENT AND TRADEMARK OFFICE
CERTIFICATE OF CORRECTION

PATENT NO. : 8,608,944 B2  
APPLICATION NO. : 12/158145  
DATED : December 17, 2013  
INVENTOR(S) : Zheng Li et al.

Page 1 of 1

It is certified that error appears in the above-identified patent and that said Letters Patent is hereby corrected as shown below:

On the Title page, item (75) of the Letters Patent, the name of the third inventor is shown as "Shuandl Hou", the correct name is "Shuandi Hou."

The patent describes its inventors as:

Inventors : Zheng Li, Beijing, (CN);
Jun Long, Beijing, (CN);
Shuandl Hou, Beijing, (CN);
Zhijian Da, Beijing, (CN);
Chaogang Xie, Beijing, (CN);
Jiushun Zhang, Beijing, (CN);
Zhanzhu Zhang, Beijing, (CN).

This should be as:

Inventors : Zheng Li, Beijing, (CN);
Jun Long, Beijing, (CN);
Shuandi Hou, Beijing, (CN);
Zhijian Da, Beijing, (CN);
Chaogang Xie, Beijing, (CN);
Jiushun Zhang, Beijing, (CN);
Zhanzhu Zhang, Beijing, (CN).

Signed and Sealed this
Fifteenth Day of April, 2014

Michelle K. Lee
*Deputy Director of the United States Patent and Trademark Office*